US00PP31565P2

(12) United States Plant Patent
Kerley et al.

(10) Patent No.: US PP31,565 P2
(45) Date of Patent: Mar. 17, 2020

(54) ***PETUNIA* PLANT NAMED 'KERTEAMORN'**

(50) Latin Name: ***Petunia* x *atkinsiana***
Varietal Denomination: KERTEAMORN

(71) Applicants: Timothy Kerley, Cambridge (GB); Sarah Kerley, Cambridge (GB); David Kerley, Cambridge (GB); Priscilla Kerley, Cambridge (GB)

(72) Inventors: Timothy Kerley, Cambridge (GB); Sarah Kerley, Cambridge (GB); David Kerley, Cambridge (GB); Priscilla Kerley, Cambridge (GB)

( * ) Notice: Subject to any disclaimer, the term of this patent is extended or adjusted under 35 U.S.C. 154(b) by 0 days.

(21) Appl. No.: 16/350,671

(22) Filed: Dec. 17, 2018

(51) Int. Cl.
*A01H 5/02* (2018.01)
*A01H 6/82* (2018.01)

(52) U.S. Cl.
USPC ..... Plt./356.1
CPC ..... *A01H 6/82* (2018.05)

(58) Field of Classification Search
USPC ..... Plt./356.21, 356.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Petunia* cultivar named 'KERTEAMORN' is disclosed, characterized by a spreading, free-branching growth habit, and bi-color medium pink flowers with a large white eye and thin light pink flower rim. Flowering begins under short day conditions. The plants flower abundantly and are more tolerant to rain than the average *Petunia*. The new variety is a *Petunia*, normally produced as an outdoor garden or container plant.

2 Drawing Sheets

Figure 1:
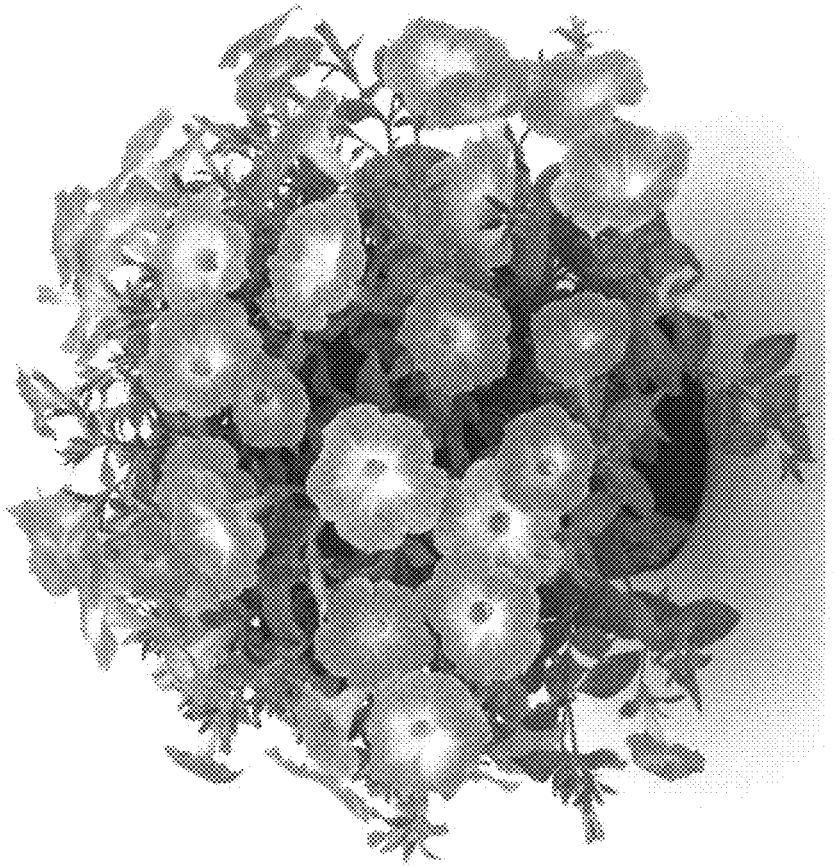

Latin name of the genus and species: *Petunia* x *atkinsiana*.

Variety denomination: 'KERTEAMORN'.

BACKGROUND OF THE INVENTION

'KERTEAMORN' is a product of a breeding and selection program for ornamental *Petunia* varieties to be vegetatively propagated. The new plant of the present invention comprises a new and distinct cultivar of *Petunia* plant.

'KERTEAMORN' is a seedling resulting from the crossing of the unpatented proprietary *Petunia atkinsiana* referred to as '11-293-15' with the pollen parent, an unpatented, proprietary, *Petunia atkinsiana* referred to as '15-572-16', conducted in August 2013. The selection of the new variety was made in May 2014, by the inventor at a research greenhouse located in Cambridge, UK. Date of first sale was Dec. 18, 2017, in the United States. This sale was made directly by the inventor or one who obtained the claimed invention directly or indirectly from the inventor. This sale and all public disclosures made before the filing of this application fall within the exception allowed under 102(b)(1).

'KERTEAMORN' was first asexually reproduced by vegetative terminal cuttings at a research greenhouse in Cambridge, UK, September 2014. The new cultivar has been found to retain its distinctive characteristics through successive asexual propagations.

SUMMARY OF THE INVENTION

The cultivar 'KERTEAMORN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERTEAMORN' These characteristics in combination distinguish 'KERTEAMORN' as a new and distinct *Petunia* cultivar:

1. Bi-color flower with medium pink and a large white eye and thin light pink flower rim.
2. Day-length neutral flowering. Flower bud initiation occurs in day lengths of less than 10 hours.
3. Spreading plant habit. 4. Very free flowering habit.
5. Medium sized *Petunia* flowers.
6. Good tolerance for rain.

PARENT COMPARISON

Plants of the new cultivar 'KERTEAMORN' are similar to plants of the seed parent in most horticultural characteristics, however, plants of the new cultivar 'KERTEAMORN' differ in the following:

1. '11-293-15' has a lighter pink flower color than 'KERTEAMORN'.

Plants of the new cultivar 'KERTEAMORN' are similar to plants of the pollen parent in most horticultural characteristics however, plants of the new cultivar 'KERTEAMORN' differ in the following:

1. 'KERTEAMORN' has a stable thin light pink flower rim, the pollen parent has an unstable picotee.
2. 'KERTEAMORN' produces flowers all over the plant, the pollen parent does not produce flowers on the top of the plant.

COMMERCIAL COMPARISON

Plants of the new cultivar 'KERTEAMORN' can be compared to the commercial variety *Petunia* 'Corona Rose Rim', unpatented. These varieties are similar in most horticultural characteristics; however, 'KERTEAMORN' differs in the following:

1. 'KERTEAMORN' produces larger flowers.
2. 'KERTEAMORN' produces shorter sepals.
3. 'KERTEAMORN' produces more flowers per plant.
4. 'KERTEAMORN' produces brighter pink flowers.

Plants of the new cultivar 'KERTEAMORN' can also be compared to the commercial variety *Petunia* 'Veranda Hot Rose', unpatented. These varieties are similar in most horticultural characteristics; however, 'KERTEAMORN' differs in the following:

1. Flower production of 'KERTEAMORN' begins under short day conditions, this comparator does not flower under short days.
2. 'KERTEAMORN' produces brighter pink flowers with a larger white eye.

BRIEF DESCRIPTION OF THE PHOTOGRAPHS

The accompanying photograph in FIG. 1 illustrates in full color a typical plant of 'KERTEAMORN' grown in a greenhouse, in Cambridge, United Kingdom.

Figure 2:
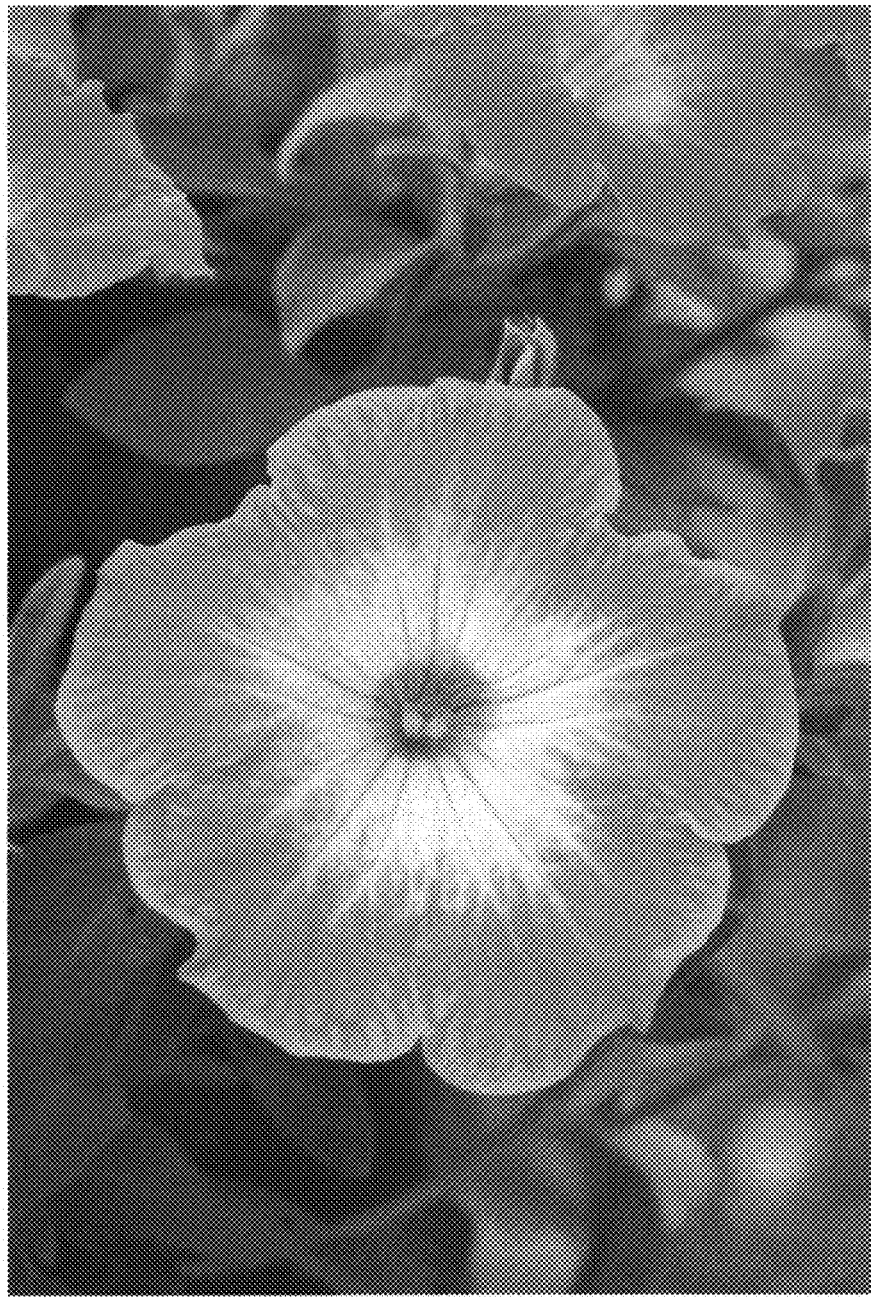

FIG. 2 illustrates in full color a typical mature flower of 'KERTEAMORN' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERTEAMORN' plants grown in greenhouse in Cambridge, United Kingdom, under natural lighting. Measurements were taken during April of 2018. The plants were approximately 16 weeks old from a rooted cutting in a 1.5 liter pot. The growing temperature ranged from 20° C. to 35° C. during the days, 17° C. to 23° C. during the nights. Measurements and numerical values represent averages of typical plant types.

Botanical classification: *Petunia atkinsiana* 'KERTEAMORN'.

PROPAGATION

Time to initiate roots: Approximately 10 days at 20° C.
Root description: Fibrous, freely branching. White, to light tan, not accurately measured with RHS chart.
Time to produce a rooted cutting: About 21 to 28 days.

PLANT

Growth habit: Spreading.
Pot size of plant described: 1.5 liter.
Height: 17.7 cm to top of flowering plane.
Plant spread: 54.3 cm.
Growth rate: Moderate.
Length of primary lateral branches: 3.9 cm.
Diameter of lateral branches: 0.5 cm.
Quantity of primary lateral branches: 5.
Characteristics of primary lateral branches:
- *Color.*—Young stem: RHS Yellow-Green 146B. Mature stem: RHS Yellow-Green 146A.
- *Texture.*—Densely pubescent.
- *Strength.*—Strong.

Internode length: 2.57 cm.

FOLIAGE

Leaf:
- *Arrangement.*—Alternate before flowering, then opposite.
- *Form.*—Simple.
- *Quantity.*—33 per main branch.
- *Average Length.*—3.8 cm.
- *Average Width.*—2.5 cm.
- *Shape of blade.*—Ovate.
- *Apex.*—Acute.
- *Base.*—Broad attenuate.
- *Margin.*—Entire. Slightly undulating.
- *Texture of top surface.*—Sparsely pubescent.
- *Texture of bottom surface.*—Sparsely pubescent.
- *Color.*—Young foliage upper side: Darker than RHS Yellow-Green 147A, 147B. Young foliage under side: RHS Yellow-Green 147B. Mature foliage upper side: RHS Yellow-Green 147A. Mature foliage under side: RHS Yellow-Green 147B.
- *Venation.*—Type: Pinnate. Venation color upper side: Between RHS Yellow-Green 146C. Venation color under side: RHS Yellow-Green 146B.
- *Petiole.*—Length: 3 mm. Diameter: 2 mm. Color: RHS Yellow-Green 146B. Texture: Upper surface sparsely pubescent, lower surface densely pubescent.

FLOWER

Natural flowering season: Spring and Summer in Cambridge, United Kingdom.
Days to flowering from rooted cutting: 21 to 28 days.
Inflorescence and flower type and habit: Simple, salverform.
Rate of flower opening: Typically about 2 days from bud to fully opened flower.
Flower longevity on plant: 7 to 8 days.
Approximate quantity of flowers per plant: Average 46 flowers and 21 buds on a plant of this age.
Persistent or self-cleaning: Self-cleaning.
Bud:
- *Shape.*—Oblong.
- *Length.*—4.5 cm.
- *Diameter at apex.*—0.9 cm.
- *Diameter at base.*—0.4 cm.
- *Texture.*—Moderately pubescent.
- *Color.*—RHS Red-Purple 70B. Central vein 146D.

Flower size:
- *Diameter.*—6 cm.
- *Length.*—About 2.23 cm.
- *Flower tube diameter at distal end.*—About 1.37 cm.
- *Flower tube diameter at proximal end.*—About 0.43 cm.

Petals:
- *Length from tube.*—2.7 cm.
- *Length of free portion.*—1.2 cm.
- *Width.*—2.7 cm.
- *Quantity.*—5.
- *Shape.*—Obovate.
- *Appearance.*—Shiny.

*Texture, upper surface.*—Glabrous.
*Texture, lower surface.*—Glabrous.
*Apex.*—Obtuse.
*Margin.*—Entire, slightly undulating.

Color:
*When opening.*—
*Upper surface.*—Eye (base before tube) Green-Yellow 1C, middle section of Red-Purple 62D with veining 1D, outer section Rede-Purple 67A becoming 67B at margin.
*Lower surface.*—Base section Red-Purple 73D becoming 73A at outer section.
*Fully opened.*—
*Upper surface.*—Eye (base before tube) Green-yellow 1C and 1D with veining of 73D. Middle section 67A becoming 67B at petal margin with veining of 68A.
*Lower surface.*—Base section near Red-Purple 67D becoming 67B at apex. Prominent central vein of Yellow-Green 144C.
*Flower tube* (*outside*).—RHS Red-Purple 73C, 73D.
*Flower tube, vein* (*outside*).—RHS Yellow-Green 144C.

Corolla tube:
*Length.*—2.23 cm.
*Diameter at distal end.*—1.37 cm.
*Diameter at proximal end.*—0.43 cm.
*Texture, inner surface.*—Glabrous.
*Texture, outer surface.*—Sparsely pubescent.
*Color, inner surface.*—Near RHS Yellow 2D, flushed Greyed-Orange 163B.

Sepals:
*Quantity per flower.*—5 fused along lower half.
*Shape.*—Cuneate.
*Length.*—2.4 cm.
*Width.*—0.57 cm.
*Margin.*—Entire, undulating to twisted.
*Apex.*—Acute.
*Texture, upper surfaces.*—Sparsely pubescent.
*Texture, lower surfaces.*—Densely pubescent.
*Color.*—Upper Surface: RHS Yellow-Green 157A. Lower Surface: RHS Yellow-Green 147B.

Peduncle:
*Strength.*—Moderate.
*Aspect.*—45 to 75 degrees to stem.
*Length.*—2.2 cm.
*Diameter.*—2 mm.
*Texture.*—Densely pubescent.
*Color.*—Near RHS Yellow-Green 146C.

Fragrance: None.

REPRODUCTIVE ORGANS

Stamens:
*Number.*—5 partially fused to inside of corolla tube.
*Length.*—2 cm.
*Filament length.*—1.3 cm free section.
*Filament color.*—RHS Green-White 157D.

Anthers:
*Length.*—2 mm.
*Shape.*—Reniform.
*Color.*—Near RHS Green-Yellow 1D.
*Pollen.*—Color: Near RHS Green-White 157C.

Pistil:
*Number.*—1.
*Length.*—2.23 cm.
*Style.*—Length: 1.73 cm. Color: RHS Yellow-Green 144B.
*Stigma.*—Shape: Linear. Color: RHS Yellow-Green 150B. Ovary Color: RHS Yellow-Green 144A.

OTHER CHARACTERISTICS

Seeds and fruits: Not observed to date.

Disease/pest resistance: Neither resistance nor susceptibility to the normal diseases and pests of *Petunia* have been observed. Typical well-known diseases include: *Botrytis cineria, Fusarium, Pythium, Phytophthora*, and *Rhizoctonia* species. Typical well-known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'KERTEAMORN' as herein illustrated and described.

* * * * *